United States Patent
Ishikawa et al.

(10) Patent No.: US 6,546,268 B1
(45) Date of Patent: Apr. 8, 2003

(54) GLUCOSE SENSOR

(75) Inventors: Akira Ishikawa, Royce City; Nabuo Takeda, Richardson; Suzanne I. Ahn; Steven R. Hays, both of Dallas; Kevin Nelson, Arlington, all of TX (US)

(73) Assignee: Ball Semiconductor, Inc., Allen, TX (US)

( * ) Notice: Subject to any disclaimer, the term of this patent is extended or adjusted under 35 U.S.C. 154(b) by 268 days.

(21) Appl. No.: 09/586,200

(22) Filed: Jun. 2, 2000

Related U.S. Application Data

(60) Provisional application No. 60/137,071, filed on Jun. 2, 1999.

(51) Int. Cl.⁷ .................................................. A61B 5/05
(52) U.S. Cl. ...................... 600/345; 600/347; 600/365; 204/403.01
(58) Field of Search .................................. 600/345, 347, 600/365; 204/403.01, 414, 415; 257/618

(56) References Cited

U.S. PATENT DOCUMENTS

| | | | |
|---|---|---|---|
| 3,944,982 A | 3/1976 | Mogi et al. ............. 340/171 R |
| 4,016,866 A * | 4/1977 | Lawton ..................... 600/348 |
| 4,333,072 A | 6/1982 | Beigel ................... 340/825.54 |
| 4,538,616 A * | 9/1985 | Rogoff ..................... 600/365 |
| 5,337,747 A | 8/1994 | Neftel ....................... 128/635 |
| 5,722,397 A * | 3/1998 | Eppstein ................... 600/345 |
| 5,786,988 A * | 7/1998 | Harari ...................... 361/749 |
| 5,837,454 A * | 11/1998 | Cozzette et al. ............... 435/6 |
| 5,877,943 A | 3/1999 | Ramamurthi ............... 361/783 |
| 5,955,776 A * | 9/1999 | Ishikawa .................... 257/618 |
| 6,001,067 A * | 12/1999 | Shults et al. ................ 600/584 |
| 6,088,608 A * | 6/2000 | Schulman et al. .......... 600/345 |
| 6,201,980 B1 * | 3/2001 | Darrow et al. ............. 600/347 |
| 6,264,611 B1 * | 7/2001 | Ishikawa et al. ........... 600/486 |
| 6,268,161 B1 * | 7/2001 | Han et al. .................... 435/14 |
| 6,285,897 B1 * | 9/2001 | Kilcoyne et al. ........... 600/350 |
| 6,326,647 B1 * | 12/2001 | Chiu ........................... 257/99 |

\* cited by examiner

*Primary Examiner*—Kevin Shaver
*Assistant Examiner*—Patricia Mallari
(74) *Attorney, Agent, or Firm*—Howison, Thoma & Arnott, L.L.P.

(57) ABSTRACT

A biochemical sensor based on ball integrated circuit technology which is designed to be biocompatible for implantation within a human or animal body. A sensor media is mounted to the ball integrated circuit, the sensor media operable for sensing biochemical molecules. An onboard communication link transmits data sensed by the sensor media from the ball integrated circuit.

20 Claims, 8 Drawing Sheets

GLUCOSE SENSOR

CROSS-REFERENCE TO RELATED APPLICATIONS

This application claims priority under 35 U.S.C. 119(e) to U.S. Provisional Patent Application Ser. No. 60/137,071 entitled "GLUCOSE SENSOR" filed Jun. 2, 1999, and is related to the following pending applications: U.S. patent application Ser. No. 09/448,781 entitled "SPHERICALLY-SHAPED BIOMEDICAL IC," filed Nov. 24, 1999; U.S. patent application Ser. No. 09/448,642 entitled "MINIATURE SPHERICAL-SHAPED SEMICONDUCTOR WITH TRANSDUCER," filed Nov. 24, 1999; and U.S. patent application Ser. No. 09/521,922 entitled "IMPLANTABLE DRUG DELIVERY SYSTEM," filed Mar. 9, 2000, each of which is hereby incorporated by reference.

TECHNICAL FIELD OF THE INVENTION

This invention is related to the field of biochemical sensors using integrated circuits. The sensors are specifically designed to be biocompatible for implantation in the human or an animal body, but may also be used in laboratory or industrial settings. The sensor communicates to either or both of a pump actuator, and to an externally located RF transmitter/receiver.

BACKGROUND OF THE INVENTION

Diabetes mellitus is a disease in which glucose levels in the patient's blood become out of balance and largely unregulated and is the leading cause of morbidity in the United States. Studies have shown that when glucose levels are tightly maintained, induced secondary pathological states such as peripheral vasculopathy, which leads to such conditions as diabetic retinopathy, neuropathy, nephropathy and amputation of extremities, are largely avoided. The level of glucose control required to inhibit these associated pathological states is typically beyond the ability of diabetic patients to regulate in their own homes. Diabetic patients are required to prick a finger multiple times a day, draw a small sample of blood, place it in a glucose sensor, and then administer themselves an appropriate injection of insulin. Patient compliance is clearly an issue. If a patient does not accurately dose their insulin levels to correspond with glucose levels, then this level of insulin therapy is insufficient to stop the progress of the above mentioned pathological conditions.

A major step forward in the fight against diabetes would be the ability to automatically monitor blood glucose levels using one or more embedded sensors which eliminate the need for frequent finger pricks. After the glucose levels were automatically sensed, the sensor should be smart enough to determine if the levels were outside a preset range. The sensor would then either send a message to the patient that their glucose levels were out of range, or in the preferred case, activate an implanted insulin pump to automatically maintain glucose levels within physiological levels.

The disclosed sensing architecture describes a device, and outlines the fabrication process of the device to make a wireless glucose sensor. Such a sensor is ideal for implantation within the human body for the control of diabetes mellitus. However, it could also be used in biotech processing plants where glucose levels are required to be maintained within a certain range, or in the veterinary market for the treatment of animals that have diabetes. Because this sensor is based on semiconductor technology, the preferred embodiment is to automatically actuate a pump to meter an appropriate dosage of insulin or to add additional glucose if levels rose above or fell below a programmable range. The disclosed sensor architecture specifically deals only with the sensor. The connection of how this sensor may interact with a pump is described in a previously submitted U.S. patent application Ser. No. 09/521,922 by Ishikawa et al., entitled "Implantable Drug Delivery Systems," filed Mar. 9, 2000, and which is hereby incorporated by reference. The sampling frequency of the glucose sensor is programmable, and is determined by the radio frequency (RF) transmitter/receiver, which is external to the sensor. In the case of implantation in the human body, the external transmitter/receiver is worn by the patient, and is ideally similar in size and appearance to a beeper or other socially acceptable device. In the case that there is no pump available, or if the pump requires maintenance, this external transmitter/receiver can be programmed to sound an audible alarm or series of various alarms. The patient would then be able to manually administer an appropriate dosage. This constant feedback to the patient would allow a much tighter control of blood glucose levels, and could potentially result in a substantial decrease in mortality and morbidity currently associated with diabetes.

The disclosed sensor system is valid for a variety of biological molecules. In particular, any biological molecule that undergoes enzymatic oxidation with the concomitant production of an acid and/or hydrogen peroxide can be detected by one or more of the disclosed embodiments as described herein. Detailed discussion focuses on glucose, for example, but it should be kept in mind that glucose is only one specific example of the multitude of applications.

SUMMARY OF THE INVENTION

The present invention disclosed and claimed herein, in one aspect thereof, comprises a biochemical sensor fabricated on a ball integrated circuit. A sensor media is mounted to the ball integrated circuit, the sensor media operable for sensing biochemical molecules. An onboard communication link transmits data sensed by the sensor media from the ball integrated circuit.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
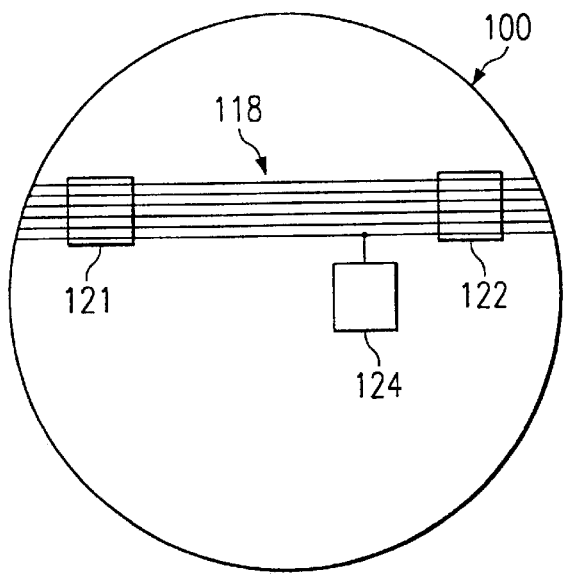
FIG. 1 illustrates a ball semiconductor sensor.

Referring now to FIG. 1, there is illustrated a ball semiconductor sensor 100 which is provided by a ball semiconductor, as described in a commonly-assigned U.S. Pat. No. 5,955,776 by Ishikawa entitled "Spherical Shaped Semiconductor Integrated Circuit," which issued Sep. 21, 1999, and is hereby incorporated by reference. The broad medical capabilities of ball semiconductors are described more fully in a previously-filed U.S. patent application Ser. No. 09/448,781 by Ishikawa et al., entitled "Spherically-Shaped Biomedical IC," filed Nov. 24, 1999, and which is hereby incorporated by reference. Briefly, the ball semiconductor 100 is approximately 1 mm or less in diameter, and is capable of receiving power from a distant source through radio frequency (RF) transmission, and sending data to an external receiver also via RF communication. They can also be physically connected to each other and to other devices. The RF signal generated by the ball semiconductor sensor 100 to carry the data stream outside the body is sufficiently strong to penetrate at least one centimeter of tissue. The ball semiconductor sensor 100 has onboard circuits comprising an RF antenna coil 118, an RF rectifier-smoother 121, an RF amplifier 122 and control logic 124.

Figure 2:
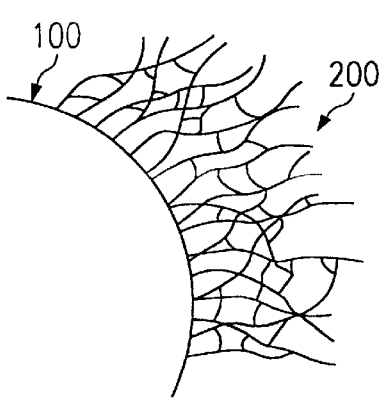
FIG. 2 illustrates a pH sensitive hydrogel covalently attached to the surface of a ball semiconductor sensor.

Referring now to FIG. 2, there is illustrated a first embodiment having a hydrogel 200 which is covalently attached to the surface of the ball sensor 100. This hydrogel 200 is pH sensitive, and undergoes very large changes in volume with small changes in local pH.

Figure 3:
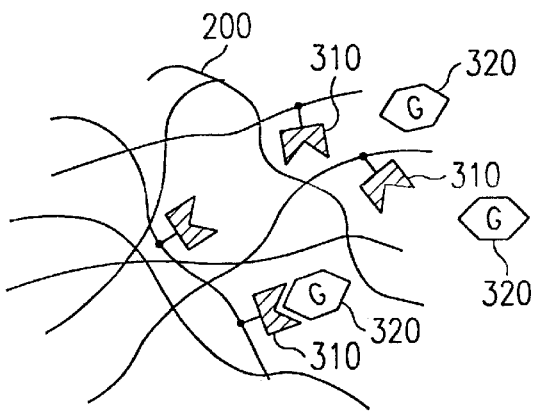
FIG. 3 illustrates the enzyme glucose oxidase attached to the hydrogel.

Referring now to FIG. 3, there is illustrated an enzyme glucose oxidase 310 attached to the hydrogel 200. The biologically active enzyme glucose oxidase 310 is covalently attached to the hydrogel 200. Glucose molecules 320 are shown disposed proximate to the hydrogel 200. This enzyme catalyzes the reaction

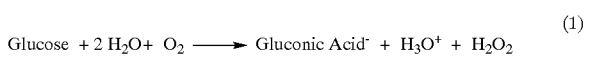

$$\text{Glucose} + 2\,H_2O + O_2 \longrightarrow \text{Gluconic Acid}^- + H_3O^+ + H_2O_2 \qquad (1)$$

Therefore, the change in acid concentration (measurable as a pH change) is directly proportional to the glucose concentration, as indicated in Equation (1). This allows the hydrogel 200 then to serve as a very sensitive glucose sensor. With the appropriate degree of cross-linking, the gel 200 can actually exert a contractile force on the ball 100 on the order of $10^4$ dynes/cm$^2$. This contractile force is large enough to be measured as a pressure exerted on the surface of the ball semiconductor 100 providing the sensor. This embodiment can therefore detect small changes in the local pH caused by the oxidation of glucose by the enzyme glucose oxidase 310. To prevent shifts in pH due to other reasons from giving a false reading, an aggregate of two or more ball sensors 100 will always be used clinically, where one of the ball sensors 100 contains the glucose oxidase 310 enzyme and the other does not. Therefore, by examining the difference between the two ball sensors 100, the effects due to the presence of glucose can be isolated.

Figure 4:
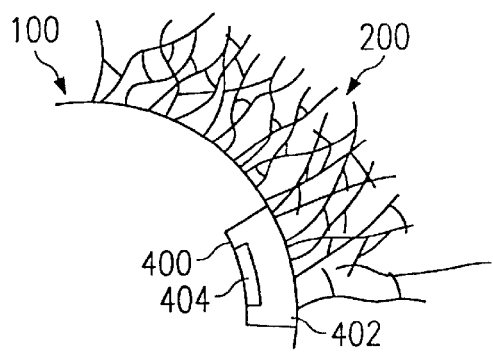
FIG. 4 illustrates the ball semiconductor with the attached hydrogel in the presence of glucose.

Referring now to FIG. 4, there is illustrated the ball semiconductor sensor 100 with the attached hydrogel 200 in the presence of glucose molecules 320. An osmotic pressure sensor 400 fabricated at or near the surface of the ball 100, and proximate to the hydrogel 200, has an osmotic chamber 402 and an electrode 404, the purposes of which will be described in greater detail hereinbelow.

Figure 5:
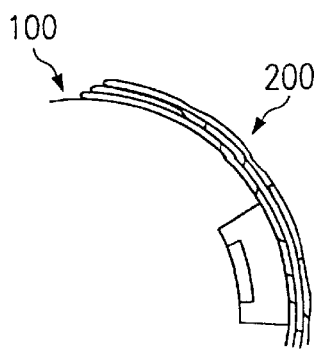
FIG. 5 illustrates the ball semiconductor with the attached hydrogel in the absence of glucose.

Refining now to FIG. 5, there is illustrated the ball semiconductor sensor 100 with the attached hydrogel 200 in the absence of glucose molecules 320. The attached hydrogel 200 is shown in a collapsed state in the presence of a changed polarity on the surface of the ball 100. The capability of changing the surface polarity of the ball 100 offers a control function over whether the ball sensor 100 can be used to either sense the presence of glucose molecules 320 when in a "blossomed" state (as indicated in FIG. 4), or can be prevented from sensing glucose molecules 320 when in a collapsed state. To accommodate this control feature, the ball sensor 100 has a polyelectrolyte hydrogel covalently attached to its surface. The polyelectrolyte is designed to collapse down tightly to the surface of the ball semiconductor 100 when the ball surface has an electrical charge of the opposite polarity as the polyelectrolyte. Conversely, when the charge on the ball 100 reverses polarity, the polyelectrolyte is repelled by the surface charge causing the hydrogel to quickly swell (or "blossom") into the aqueous environment, and thereby promoting sensing of the designated chemical(s) in the surrounding environment. In this way, the sensing function is turned on and off with each change in the surface charge.

Figure 6:
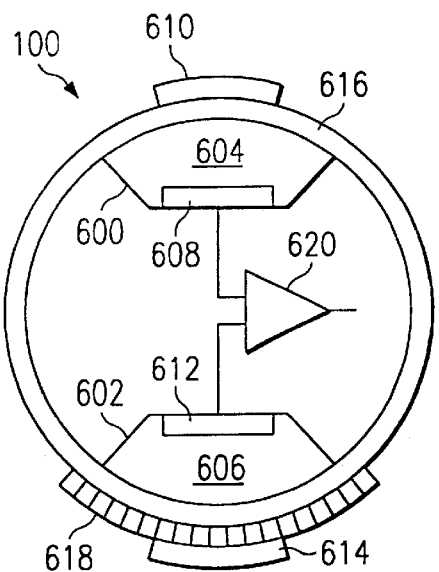
FIG. 6 illustrates a ball semiconductor sensor that has at least two osmotic pressure sensors located on the same ball sensor.

Referring now to FIG. 6, there is illustrated a ball semiconductor sensor 100 that has at least two osmotic capacitive pressure sensors 600 and 602 having respective osmotic chambers 604 and 606. Osmotic chamber 604 has a first inner electrode 608 formed at its base, and a first outer electrode 610 formed on the surface of the ball 100. Osmotic chamber 606 has a second inner electrode 612 formed at its base, and a second outer electrode 614 formed on the surface of the ball 100. A first thin polymer semipermeable membrane 616 which is permeable to small molecules including both water, salts, and glucose, covers the entire surface of the ball 100. This first polymer film 616 is permeable to small molecules including water, glucose and salts. A second semipermeable polymer film membrane 618 is applied over the osmotic pressure well 606. The second membrane 618 overlies the first membrane 616, and underlies the second outer electrode 614. This second polymer film 618 is permeable to water and salts, but not to glucose. Therefore, well 606 contains water and salts, but no glucose, and well 604 contains water, salts, glucose, and other small molecules.

The two outer electrodes 610 and 614 are disposed on the outer periphery of the ball sensor 100, with the first outer electrode 610 connected to the first membrane 616, and the second membrane 618 interstitial to the first semipermeable membrane 616 and the second outer electrode 614. The first outer electrodes 610 is applied to the top of the first polymer film 616 over the osmotic pressure well 604, and the second outer electrode 614 is applied to the top of the second polymer film 618 over the osmotic pressure well 606. The inner electrode 608 of the pressure sensor 600 connects to an input of a differential amplifier 620. Similarly, the second inner electrode 612 connects another input of the differential amplifier 620. As the contents of the osmotic pressure wells 604 and 606 change, the corresponding osmotic pressure and conductivity changes effect a change in the capacitance between the two sets of electrode pairs (608/610 and 612/614). By sending the output of these two capacitors 600 and 602 into the differential amplifier 620, the output voltage will be proportional to the concentration of glucose being measured.

Figure 7:
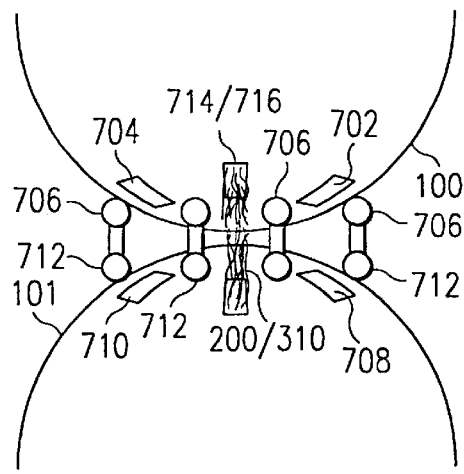
FIG. 7 illustrates two ball sensors in a cluster with electrodes placed at precise locations near the bumps that connect the two ball sensors.

Referring now to FIG. 7, there is illustrated two ball sensors 100 and 101 disposed in a cluster. Ball sensor 100 includes a cathode 702, an anode 704 and one or more interconnect bumps 706. Similarly, ball sensor 101 includes a cathode 708, an anode 710 and one or more interconnect bumps 712. The bumps 706 and 712 electrically interconnect each of the balls sensors 100 and 101 when configured into a cluster. Notably, the ball 100 (or ball 101) may have several sets of interconnect bumps 706 strategically placed in various quadrants of the sphere of the ball 100 to facilitate interconnection to adjoining balls. Ball 100 has a hydrogel 714 and enzyme glucose oxidase 716 combination (similar to hydrogel 200 and glucose oxidase 310) disposed in selected areas thereon, and ball 101 also has a hydrogel 718 and enzyme glucose oxidase 720 combination (similar to hydrogel 200 and glucose oxidase 310) disposed in selected areas thereon. As mentioned hereinabove, where a cluster of balls 100 are used, one of the balls 100 (or 101) may not incorporate the oxidase 310 in order to provide a reference against that parameter which is being measured, in this case, glucose.

Figure 8:
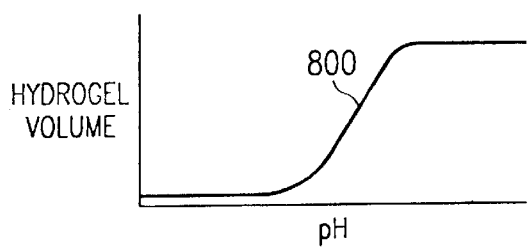
FIG. 8 illustrates a graph indicating the volume of the hydrogel as a function of the change in pH.
Figure 9:
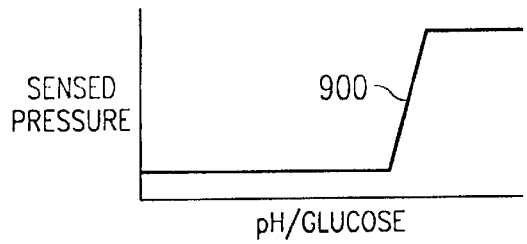
FIG. 9 illustrates a corresponding graph showing the anticipated sensed pressure as a function of pH changes, which will be proportional to graphing pressure changes as a function of glucose concentration if glucose oxidase is attached to the hydrogel.

Referring now to FIGS. 8 and 9, there are illustrated graphs indicating the volume of the hydrogel 200 as a function of the change in pH (in FIG. 8), and a graph showing the anticipated sensed pressure as a function of pH changes (in FIG. 9), which will be proportional to graphing pressure changes as a function of glucose concentration if glucose oxidase 310 is attached to the hydrogel 200. Because of the rapid rate of change of volume with respect to pH, this embodiment provides near step function output signals 800 and 900, as shown in FIGS. 8 and 9. Therefore, this sensor 100 is ideal to drive an insulin pump, giving sharp on/off signals to the pump mechanism.

Figure 10:
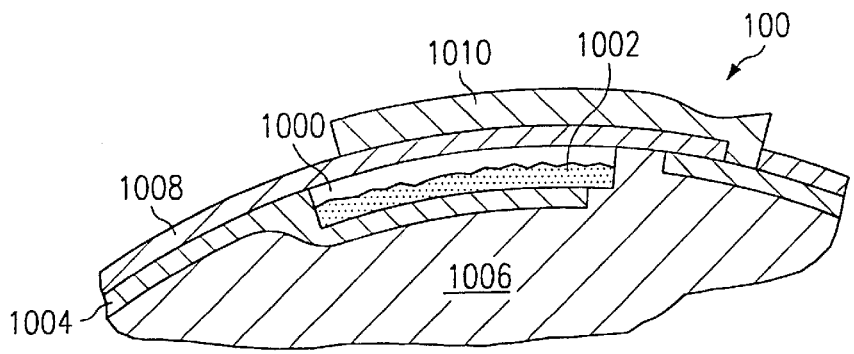
FIG. 10 illustrates a ball semiconductor sensor having a well for electrochemical detection of glucose using a pH sensitive hydrogel coupled with an electrically conductive polymer.

Referring now to FIG. 10, there is illustrated a ball semiconductor sensor 100 having a well (or chamber, similar to chambers 604 and 606) 1000 for electrochemical detection of glucose using a pH sensitive hydrogel coupled with an electrically conductive polymer. A polymer composite 1002 placed in the well 1000 consists of the pH-sensitive hydrogel 200, an electrically conductive polymer, and the enzyme glucose oxidase 310. The pH-sensitive hydrogel 200 is cross-linked with the electrically conductive polymer composite 1002 (e.g., polyaniline) that also swells in water. The enzyme glucose oxidase 310 is covalently attached to this polymer composite 1002, which is then attached to the surface of an inner electrode 1004 (similar to inner electrodes 608 and 612) at the bottom of the well 1000 at the surface of the semiconductor substrate 1006. A semipermeable membrane 1008 (similar to the first membrane 616) is attached across the top of the well 1000, forming the tightly sealed electrochemical chamber 1000.

An outer electrode 1010 (similar outer electrodes 610 and 614) and the inner electrode 1004 together form a parallel plate capacitor. The outer electrode 1010 is attached to the semipermeable membrane 1008, forming the parallel plate capacitor, which is connected to an LRC circuit (not shown in FIG. 10). The LRC circuit preferably detects changes in glucose levels by shifts in the natural frequency of the circuit. As glucose diffuses into the chamber 1000, it will react with the glucose oxidase 310, change the pH within the chamber 1000, and hence change the volume of the hydrogel composite 1002. As the volume of the hydrogel composite 1002 changes, the electrically conducting polymer is brought nearer to the top outer electrode 1010. This changes the effective capacitive distance, which is detected as a change in the frequency of the LRC circuit. Therefore, changes in the glucose level are directly measured as frequency changes in the electronic circuitry of the semiconductor.

In another embodiment, the relative change in osmotic pressure is utilized as a sensitive measure of glucose concentration, as demonstrated in U.S. Pat. No. 5,337,747 by Neftel, entitled "Implantable Device For Estimating Glucose Levels," and issued Aug. 16, 1994. It has been shown that the major changes in the contents of the interstitial fluid involve a limited number of substances, one of which is glucose. Furthermore, it has been shown that interstitial glucose levels closely follow blood glucose levels. Therefore, the relative osmotic pressure through a semipermeable membrane that allows glucose to pass with respect to a semipermeable membrane that excludes glucose will provide an accurate measure of the interstitial glucose level. Using two membranes will control for changes in interfering substances, changes in patient hydration states and other confounding situations.

In another embodiment, a platinum sensor is attached to the surface of the ball. This electrode amperometrically senses the concentration of hydrogen peroxide generated as per Equation (1) above. Once hydrogen peroxide is generated, it is electrochemically detected according the formula of Equation (2):

$$H_2O_2 \longrightarrow O_2 + 2H^+ 2e^- \tag{2}$$

at +600 mV vs Ag/AgCl. Therefore, the current generated is proportional to the amount of hydrogen peroxide generated, which is proportional to the glucose concentration. The problem with this approach is the presence of interfering substances such as ascorbic acid, dopamine, acetaminophen and uric acid. To help with selectivity, a 3-mercaptopropyltrimethoxysilane coating is applied to the platinum. The enzyme glucose oxidase is then immobilized on the mercaptosilane. This is then coated with a semipermeable membrane such as polyurethane. A silver electrode is treated in a similar manner but without enzyme immobilization to serve as a reference.

Figure 11:
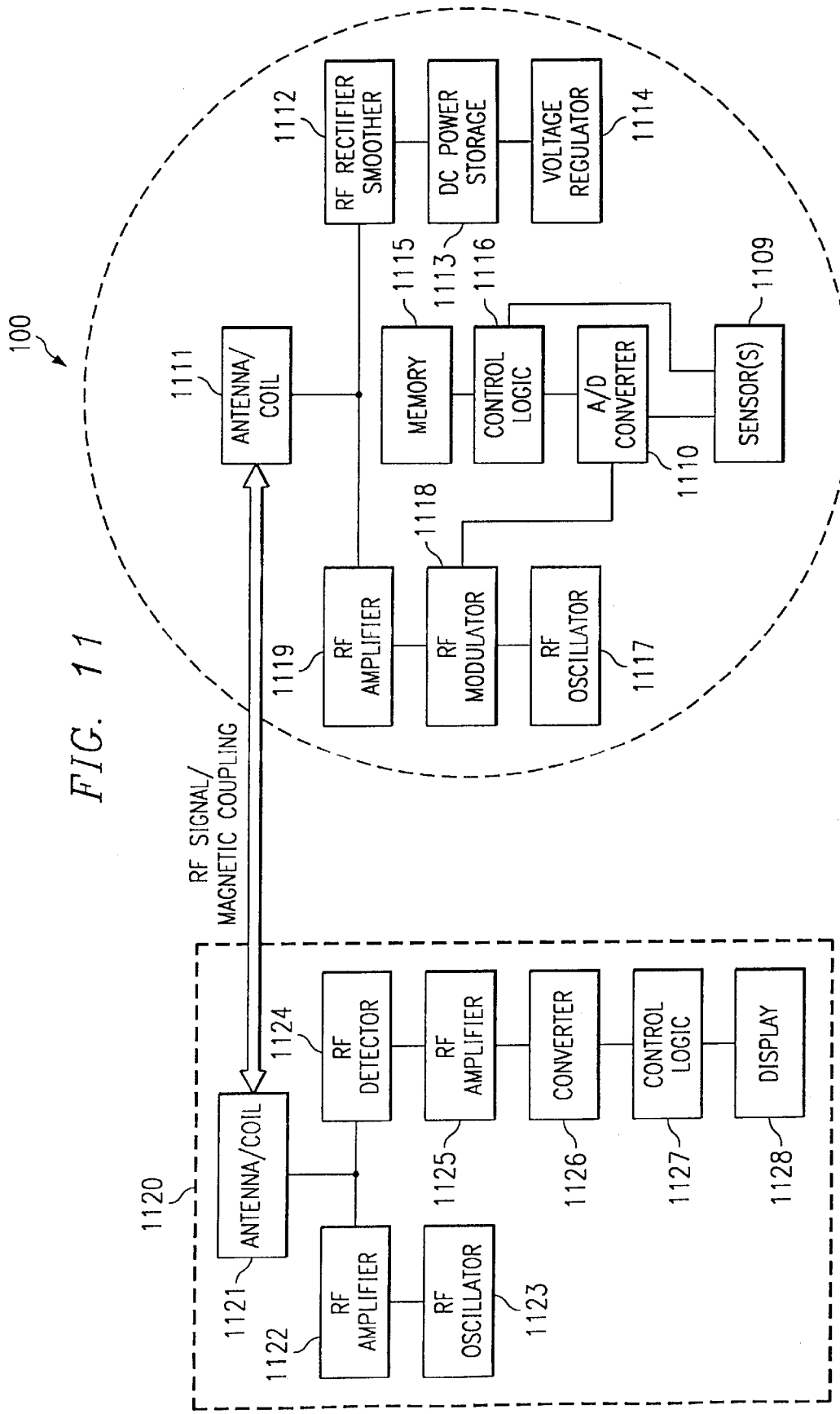
FIG. 11 illustrates a block diagram of a ball sensor with an integral transducer in combination with a radio frequency communication system in accordance with the present invention.

Referring now to FIG. 11, there is illustrated the basic circuit functions of the ball sensor 100. The spherical semiconductor ball 100 is provided having a substrate upon which the transponder circuitry is disposed, and includes an antenna/coil 1111, which serves the dual purpose of receiving signal energy from a remote central processing unit 1120 and transmitting signal energy thereto. The signal energy may be received by the antenna/coil 1111 by inductive coupling if the central processing unit 1120 is sufficiently close to the ball 100. Alternatively, electromagnetic waves can be used to transmit power from the central processing unit 1120 to the ball 100, whereby the magnetic field component of the electromagnetic wave induces a current in the coil 1111, in accordance with known techniques. The power signal received by the antenna/coil 1111 is rectified and smoothed by an RF rectifier smoother circuit 1112. The output of the rectifier circuit 1112 is connected to a DC power storage device 1113, such as a capacitor. Such capacitor might also perform a waveform smoothing function. A voltage regulator 1114 is used to make the DC voltage stable regardless of the distance between the central processing unit 1120 and the ball 100.

An RF oscillator 1117 generates an RF carrier signal at a predetermined frequency in the RF band. An RF modulator 1118 modulates onto the carrier frequency signal one or more of the sensor data corresponding sensor(s) 1109 via an analog-to-digital (A/D) converter 1110, and information from a memory 1115 which has stored therein an ID code as a digital word. Notably, the memory 1115 may have the capacity to store more information, such as the date, time, patient name and address, physician name, etc., to facilitate the recording of pertinent patient/doctor information. The resulting modulated signal is amplified by an RF amplifier 1119, and then transmitted to the outside through the antenna/coil 1111. Further details of the preferred coil are described in the aforementioned commonly assigned U.S. patent application Ser. No. 09/448,642 by Ishikawa et al., entitled "Miniature Spherical-Shaped Semiconductor With Transducer" and filed Nov. 24, 1999.

The external central processing unit 1120 includes an antenna/coil 1121 that serves the dual purpose of generating the electromagnetic wave for transmitting power to the ball 100, and receiving the RF data signal transmitted by the ball 100. It is preferred that the frequency of the electromagnetic wave that is output by the antenna/coil 1121 is different from the carrier frequency generated by the RF oscillator 1117. An RF amplifier 1122 is used to couple the electromagnetic wave for power transmission to the antenna/coil 1121. An RF oscillator 1123 determines the frequency of the electromagnetic wave that is emitted by the central processing unit 1120. The data received by the antenna/coil 1121 is detected by an RF detector 1124 and then amplified by an RF amplifier 1125. Preferably, the converter 1126 converts the signal from the RF amplifier 1125 to a digital signal, which in turn is input to control logic 1127. The control logic 1127 may be a smaller central processing unit which interfaces with another main processor of the main central processing unit 1120. The control logic 1127 extracts the data from the signal received by the central processing unit 1120 from the ball 100 and displays that information on a suitable display 1128, such as a CRT screen.

The technique for transmitting data from the ball 100 to the main central processing unit 1120 using the carrier frequency generated by the RF oscillator 1117 can be in the form using any suitable protocol. The modulation can be AM, FM, PM, or any other suitable modulation technique.

Figure 12:
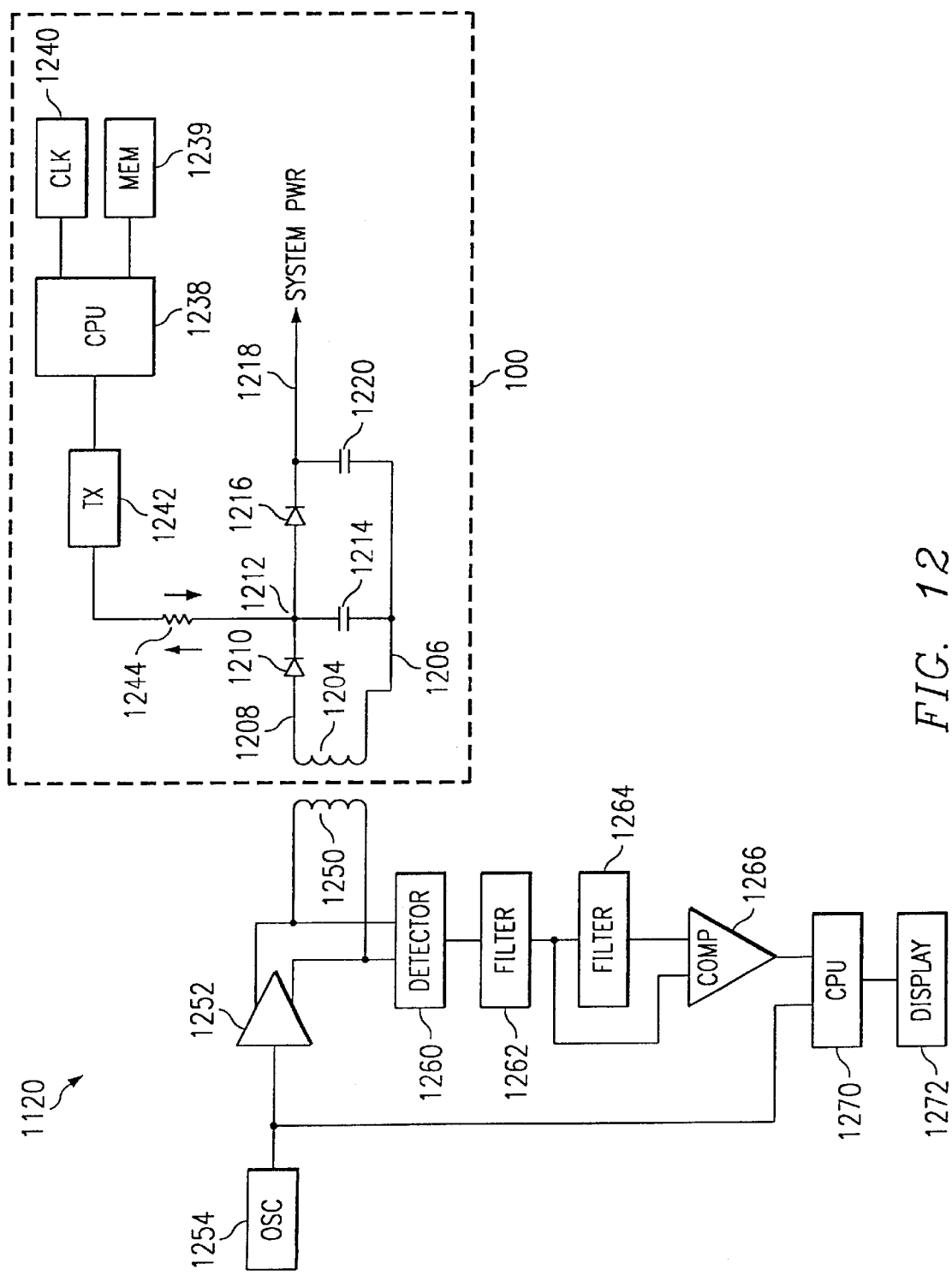
FIG. 12 illustrates a schematic block diagram of the receiver/transmitter and a detection/power system.

Referring now to FIG. 12, there is illustrated a schematic block diagram of the ball sensor 100 and the remote system for the powering/detection operation. The illustrated embodiment of FIG. 12 is that associated with a "passive" system, which term refers to the fact that there is no battery associated therewith. In order to operate the system, there is provided an inductive coupling element 1204 in the form of an inductor, which is operable to pick up an alternating wave or impulse via inductive coupling and extract the energy therein for storage in the inductive element 1204. This will create a voltage across the inductive element 1204 between a terminal 1206 and a terminal 1208. A diode 1210 is connected between the node 1208 and a node 1212, with the anode of diode 1210 connected to node 1208 and the cathode of diode 1210 connected to a node 1212. Typically, the diode 1210 will be fabricated as a Schottky diode, but can be a simple PN semiconductor diode. For the purposes of this embodiment, the PN diode will be described, although it should be understood that a Schottky diode could easily be fabricated to replace this diode 1210. The reason for utilizing a Schottky diode is that the Schottky diode has a lower voltage drop in the forward conducting direction.

The diode 1210 is operable to rectify the voltage across the inductive element 1204 onto the node 1212, which has a capacitor 1214 disposed between node 1212 and node 1206. Node 1212 is also connected through a diode 1216 having the anode thereof connected to node 1212 and the cathode thereof connected to a node 1218 to charge up a capacitor 1220 disposed between node 1218 and 1206. The capacitor 1220 is the power supply capacitor for providing power to the ball sensor 100.

A CPU 1238 and a clock circuit 1240 are provided for providing processing and timing functions to the system. A memory 1239 (similar to memory 1115) is provided in communication with the CPU 1238 for storage of an ID unique to the ball sensor 100 to allow the CPU 1238 to retrieve this information for transmittal back to the remote location 1120. This retrieval is automatic when the system is powered up and is continuous as long as the system is powered. This memory 1239 is non-volatile, such as a ROM, or it could be a programmable non-volatile memory.

In order to communicate with the CPU 1238 for transferring data therefrom, a transmit circuit 1242 is provided for interfacing to node 1212 through a resistive element 1244. This allows energy to be transmitted to node 1212. It is important to note that the semiconductor junction across diode 1210 is a capacitive junction. Therefore, this will allow coupling from node 1212 to node 1204. Although not illustrated, this could actually be a tuned circuit, by selecting the value of the capacitance inherent in the design of the diode 1210. In any event, this allows an RF connection to be provided across diode 1210 while allowing sufficient energy to be input across inductive element 1204 to provide a voltage thereacross for rectification by the diode 1210 and capacitor 1214. Typically, the frequency of this connection will be in the MHz range, depending upon the design. However, many designs could be utilized. Some of these are illustrated in U.S. Pat. No. 4,333,072 by Beigel, entitled "Identification Device" issued Jun. 1, 1982, and U.S. Pat. No. 3,944,982, by Mogi et al., and entitled "Remote Control System For Electric Apparatus" issued Mar. 16, 1982, both of which are hereby incorporated by reference. With these types of systems, power can continually be provided to the node 1212 and subsequently to capacitors 1214 and 1220 to allow power to be constantly applied to the ball sensor 100.

The remote system 1120 includes an inductive element 1250 which is operable to be disposed in an area proximate to the ball sensor 100. The inductive element 1250 is driven by a driving circuit 1252 which provides a differential output that is driven by an oscillator 1254. This will be at a predetermined frequency and power level necessary to couple energy from inductive element 1250 to inductive element 1204. Since the remote system 1120 is an external system, the power of the oscillator 1254 can be set to a level to account for any losses encountered in the scanning operation.

When the information is received from the ball sensor 100, it is superimposed upon the oscillator signal driving the inductive element 1250. This is extracted therefrom via a detector 1260 which has the output thereof input to a first low pass filter 1262 and then to a second low pass filter 1264. The output of low pass filters 1262 and 1264 are compared with a comparator 1266 to provide the data. The filter 1262 will provide an average voltage output, whereas the filter 1264 will provide the actual digital voltage output. The output of the comparator 1266 is then input to a CPU 1270 which also is powered by the oscillator 1254 to process the data received therefrom. This can be input to a display 1272.

Figure 13A:
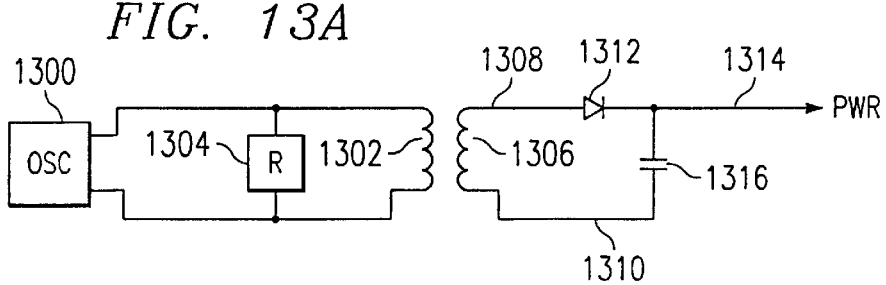
FIGS. 13A and 13B illustrate alternative embodiments for the receiver/transmitter and the storage capacitors associated therewith.
Figure 13B:
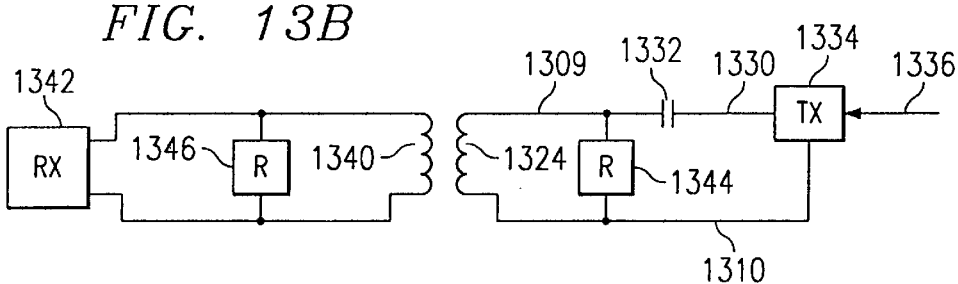

Referring now to FIGS. 13A and 13B, there are illustrated alternate embodiments for the transmit/receive operation. In FIG. 13A, there is provided an oscillator 1300 which drives an external inductive element 1302. Typically, there is some type of load 1304 disposed across the inductive element 1302. This is the primary power that is provided to the system. A separate inductive element 1306 is provided on the ball sensor 100, for being inductively coupled to the inductive element 1302. Thereafter, a voltage is generated across the inductive element 1306, the inductive element 1306 being connected between a node 1308 and 1310. A diode 1312 is connected between node 1308 and a power node 1314, and a power supply capacitor 1316 is disposed between node 1314 and node 1310. This allows the voltage on node 1306 to be rectified with diode 1312.

The receive operation in this embodiment in FIG. 13B utilizes a separate inductive element or antenna 1324 in the ball sensor 100, which is operable to be connected between nodes 1309 and 1310. Node 1309 is capacitively coupled to a transmit node 1330 with a capacitor 1332, the capacitor 1332 being a coupling capacitor. A transmitter 1334 is provided for transmitting received data from a line 1336 to the node 1330 which is then coupled to the node 1309 to impress the RF signal across the inductive element 1324.

A corresponding inductive element 1340 is disposed on the external remote controller, which inductive element 1340 is operable to be disposed proximate to the inductive element 1324. The inductive element 1340 is basically a "pick-up" element which is operable to receive information and function as an antenna and provide the received signal to a receiver 1342. The structure of FIG. 13b is a separate structure, such that node 1309 is isolated from node 1308, the power receiving node. However, it should be understood that any harmonics of the oscillator 1300 would, of course, leak over into the inductive element 1306. This can be tuned out with the use of some type of tuning element 1344 on the ball sensor 100 disposed across inductive element 1324 and also a tuning element 1346 disposed across the inductive element 1340, i.e., the antenna.

Figure 14:
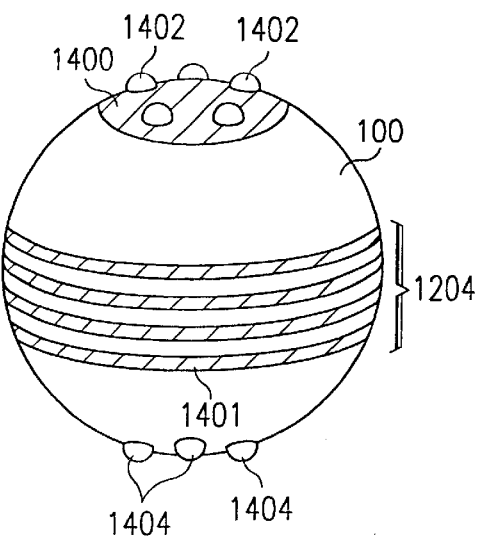
FIG. 14 illustrates a perspective view of one of the ball sensor semiconductor spheres having antenna leads disposed thereon.

Referring now to FIG. 14, there is illustrated a perspective view of the spherical IC embodiment of the ball sensor 100, wherein the inductive element 1204 is illustrated as being strips of conductive material wrapped around the exterior of the spherical ball IC 100. The inductive element 1204 described hereinabove with respect to FIG. 12, is formed of a conductive strip 1401 wrapped many times around the spherical ball sensor 100. The length of these wires depends upon the receive characteristics that are required. As described hereinabove with reference to FIGS. 13A and 13B, there could be multiple conductive strips 1401, each associated with a receive function, a transmit function or a power function, or they could all share one single conductive element or strip. On one end of the spherical ball sensor 100, there is provided an interconnect pad 1400 and conductive interconnect balls 1402 associated therewith of material such as gold. On the other end thereof are provided additional interfacing interconnect balls 1404. These interconnect balls 1402 and 1404 allow the spherical IC ball sensor 100 to be clustered with other spherical ICs. The contacts or interconnect balls 1402 and 1404 and the clustering operation are described in U.S. Pat. No. 5,877,943 by Ramamurthi, entitled "Clustering Adapter For Spherical Shaped Devices" issued Mar. 2, 1999, and assigned to the present assignee, which is hereby incorporated by reference.

Figure 15:
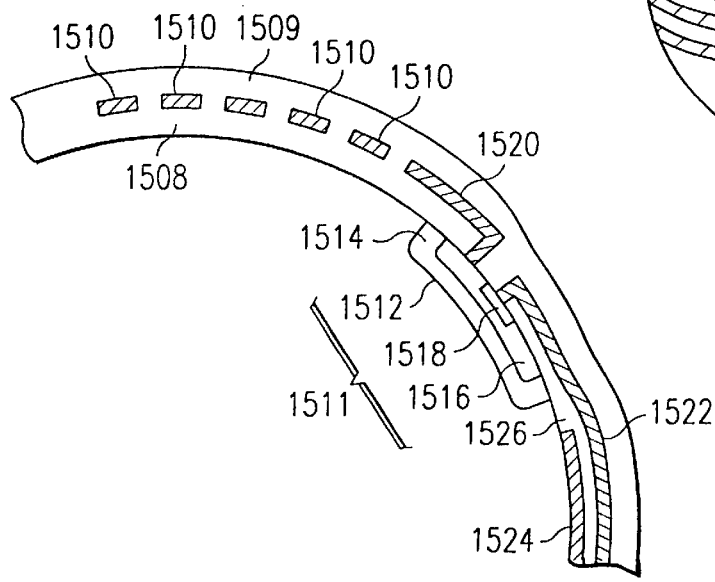
FIG. 15 illustrates a cross-sectional diagram of the portion of the surface of the ball sensor spherical IC of FIG. 14.

Referring now to FIG. 15, there is illustrated a cross-sectional diagram of the surface of the spherical IC ball sensor 100 illustrating the conductive strips forming the inductive element 1204. The conductive strips are referred to by reference numeral 1510 which are spaced on or near the surface of the IC ball sensor 100 by a predetermined distance and separated therefrom by a layer of silicon dioxide 1508. A passivation layer 1509 is then disposed over the upper surface of the conductive strips 1510. The conductive strips 1510 can be fabricated from polycrystalline silicon but, it would be preferable to form them from the upper metal layer to result in a lower conductivity strip. This will allow the strips 1510 to be narrower and separated from each other by a larger distance. This separation would reduce the amount of capacitance therebetween.

One end of the strips 1510 is connected to a diode structure 1511. The diode structure 1511 is formed of an N-well implant region 1514 having an interface 1512 with the underlying substrate, and into which a P-well implant region 1516 is disposed, and an N-well implant region 1518 disposed within the P-well implant region 1516. This forms a PN diode where one end of the conductive strips 1510, a conductive connection 1520, is connected to the P-well 1516 implant region, and a conductive layer 1522 is connected at one end to the N-well implant region 1518. This conductive layer or strip 1522 extends outward to other circuitry on the integrated circuit and can actually form a capacitor (e.g., capacitors 1214 or 1220). Since it needs to go to the capacitor directly, a lower plate 1524 formed of a layer of polycrystalline silicon or metal in a double-metal process, could be provided separated therefrom by a layer of oxide 1526.

Figure 16:
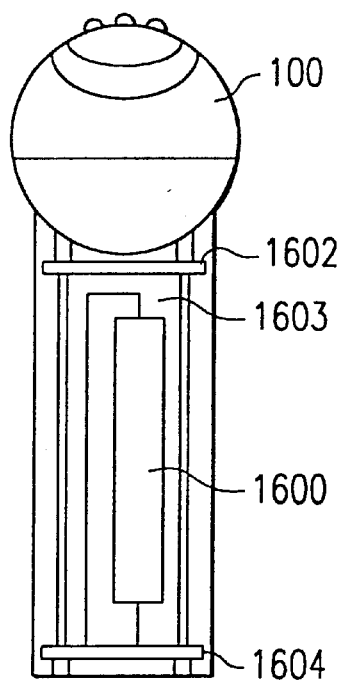
FIG. 16 illustrates a side view of an alternative embodiment utilizing additional circuitry or structure attached to the ball IC for providing a local power source.

Referring now to FIG. 16, there is illustrated a side view of an alternative embodiment utilizing additional circuitry or structure attached to the ball IC 100 for providing a local power source. As described hereinabove, the ball IC 100 requires a power-generating structure for storing a power supply voltage such that diodes must be provided for receiving and rectifying a large amount of power and charging up a power supply capacitor. Alternatively, the ball IC 100 could be configured to interface to an attached local power supply system 1600 comprising either a battery or a capacitor. The local power supply system 1600 is illustrated as disposed on a circuit board 1603 defined by supporting structures 1602 and 1604. The circuit board 1603 contains electronics for interfacing the local power supply system 1600 to the ball IC 100.

Figure 17:
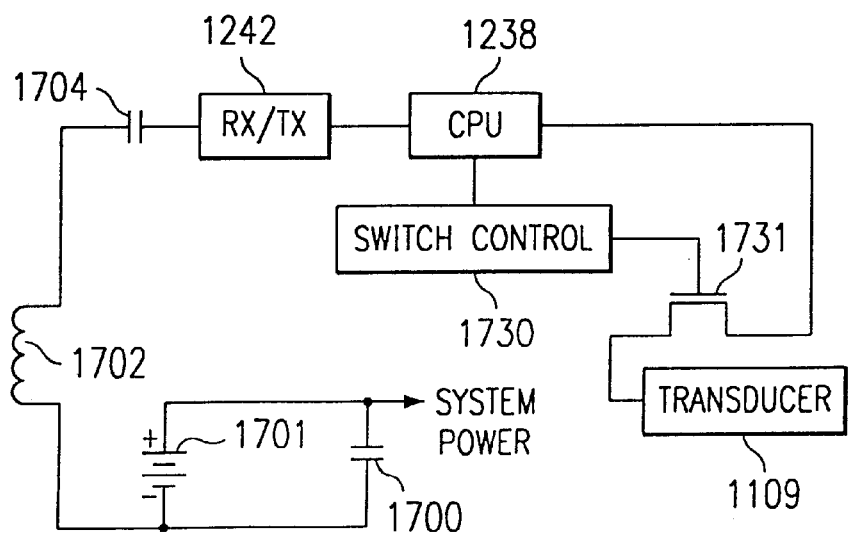
FIG. 17 illustrates a schematic block diagram of the ball IC using a battery as the local power supply system.

Referring now to FIG. 17, there is illustrated a schematic block diagram of the ball IC 100 using a battery as the local power supply system 1600. A battery 1701 (or local power source similar to 1600) is provided as a source of self-contained power and is connected across a capacitor 1700 to provide smoothing of any power output to the system power-consuming elements of the ball IC 100. Power for all onboard components is obtained from the SYSTEM POWER output by providing sufficient charge to the capacitor 1700. The capacitor 1700 could be formed on the surface of the ball IC 100 or it could actually be part of the battery structure 1701. Additionally, the capacitance 1700 could actually be the capacitance of the battery 1701. Additional structure could be provided for powering the CPU 1238 and the other circuitry on the ball IC 100 from the battery 1701. As such, there would only be required a smaller inductive element 1702 (similar to inductive element 1204) and a capacitor 1704 to allow the receive/transmit block 1242 to receive/transmit information from and to the remote exterior control station 1120. A switch control 1730 controls the gate of a switching transistor 1731 to switch the output of the transducer 1109 through the switching transistor 1731 source/drain path to the CPU 1238.

Each of the above-described sensing techniques can be implemented on the same system of printed integrated circuits. This system comprises one or more physical semiconductors that are connected into a single unit. This expands the capabilities of the described systems in two ways. First, a single biological molecule can be detected by more than one sensor, using different sensing mechanisms. This has the advantage that if one or more different types of sensors begin to degrade in performance with time, that sensor's performance can be monitored. If needed, that sensor can either be uncoupled from the system, in the case of sensor failure, or it can be re-calibrated in situ based upon the readings of other sensors, whose readings are considered stable, or by an outside sensor brought in specifically for the purpose of re-calibration. The second advantage of combining various sensing techniques, is the ability to sense several different biological molecules at the same time. This multi-chemical biosensor has the ability to take general health status readings, and flag chemical imbalances.

Figure 18:
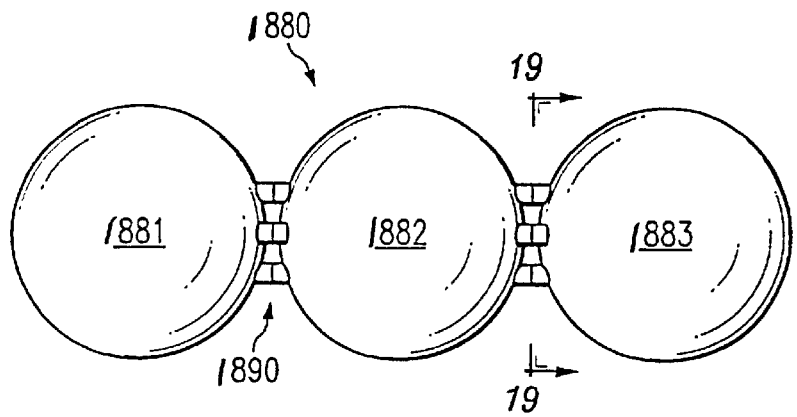
FIG. 18 illustrates a side elevation of a cluster of semiconductor balls that may be employed in a sensor function, according to a disclosed embodiment.

Referring now to FIG. 18, there is illustrated a side elevation of a cluster 1880 of semiconductor balls that may be employed in a sensor function, according to a disclosed embodiment. Although a single ball can include the foregoing functions, more complex monitoring functions with multiple sensors (or transducers) can be implemented. For example, the cluster 1880 can include a ball 1881 for power receiving and data transmission functions. Alternatively, ball 1881 can be a miniature battery. A ball 1882 can include a first transducer function, such as glucose sensing, and a ball 1883 can include a second transducer function, such as measuring pH, $pO_2$, $pCO_2$, or temperature, as the particular application requires. Connections between the balls are made through metal contacts 1890, which may be solder bumps.

Figure 19:
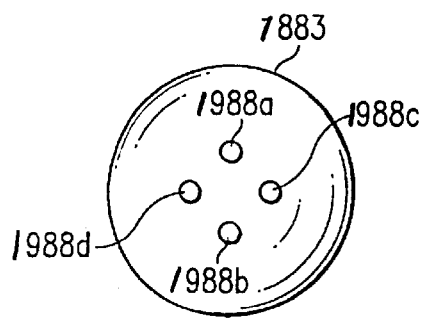
FIG. 19 illustrates a cross section taken along the line 19—19 of FIG. 18 to expose the four contacts between two balls.

Referring now to FIG. 19, there is illustrated a cross section taken along the line 19—19 of FIG. 18 to expose the four contacts 1988*a*, 1988*b*, 1988*c* and 1988*d* between ball 1882 and ball 1883. The contacts 1988*a* and 1988*b* may be power contacts, such as a positive 3.0 volts and ground, which can be passed from ball 1881 around ball 1882 by conductors on its surface using two of a group of similar contacts (designated collectively by numeral 1890 in FIG. 18). The contacts 1988*c* and 1988*d* may be data and control contacts for communications between ball 1882 and ball 1883. Similarly, data and control contacts may exist among contact group 1890 between ball 1881 and ball 1882 to the extent needed.

Figure 20:
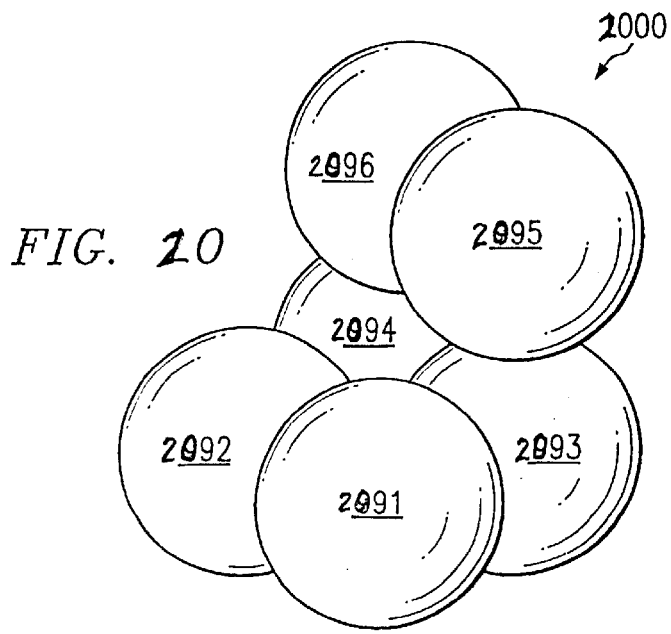
FIG. 20 illustrates a cluster or aggregation of balls.

Referring now to FIG. 20, there is illustrated a cluster or aggregation 2000 of balls 2091, 2092, 2093, 2094, 2095 and 2096, as an example of the versatility of such ball systems. The cluster 2000 specifically shows six balls arranged in a three-dimensional configuration. It will be appreciated that various other cluster arrangements are possible, limited only by the constraints of the end-use application. Each of the balls of the cluster 2000 can perform different electronic functions and communicate with each other through contacts as described above in connection with FIGS. 18 and 19. For example, ball sensors can be located on the sides of catheters to measure various parameters. More than one of the balls in the cluster 2000 can also be operable to perform a glucose sensing function. Clustered balls are able to integrate, transmit, and receive more complex information or actuate a response (emit laser, infrared, ultrasound, or electrical energy). The actuators may contain a piezoelectric driver attached to a ball surface for ultrasound generation and control for measurements of luminal diameter and fluid flow rate within the vessel lumen. Such actuators can serve as an emitting device allowing for external detection to determine location or position.

Figure 21:
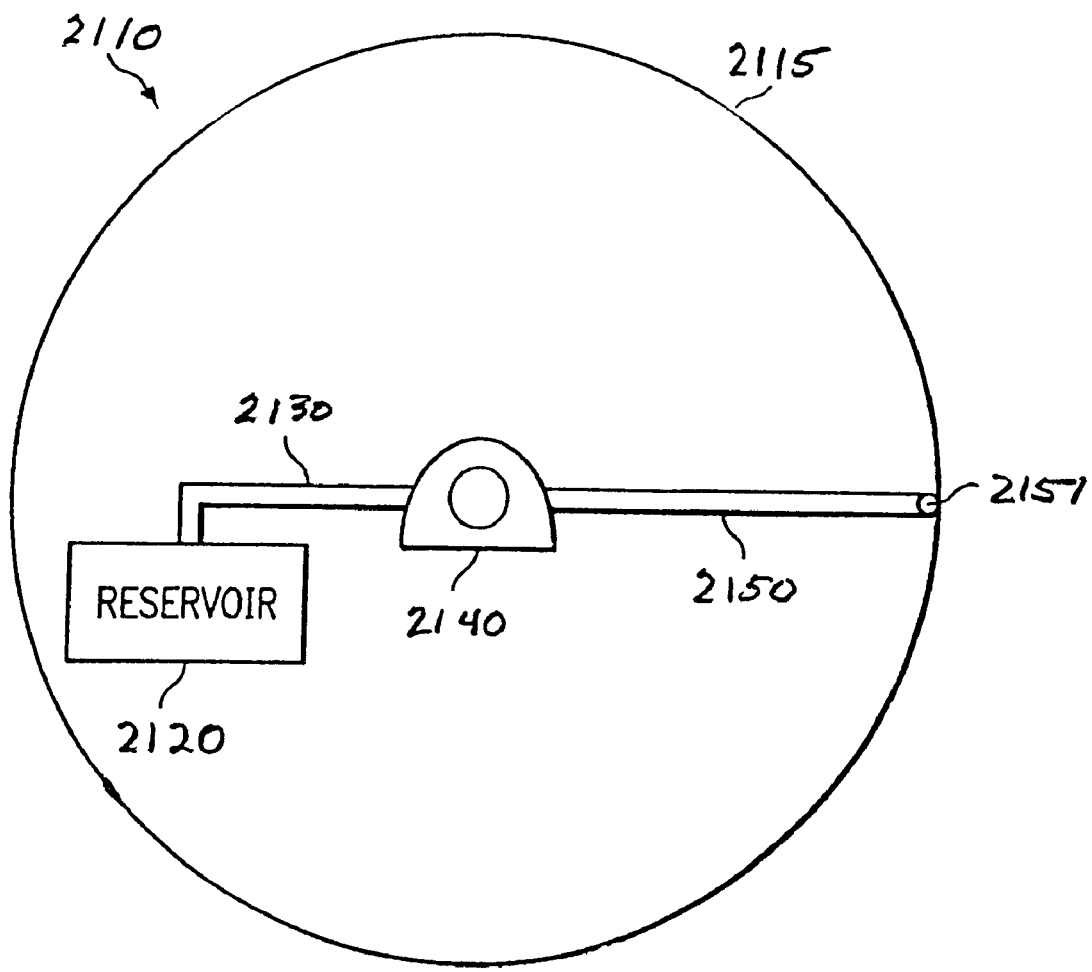
FIG. 21 illustrates an embodiment where a ball IC is constructed with a pump that is connected on one end through plumbing to reservoir, and on a second end through plumbing to the surface of the ball IC.

Referring now to FIG. 21, there is illustrated one embodiment where a ball IC 2110 is constructed with a pump 2140 that is connected on one end through plumbing 2130 to reservoir 2120, and on a second end through plumbing 2150 to the surface 2115 of the ball IC 2110. A medicine or substance (e.g., glucose) carried by the ball IC 2110 in reservoir 2120 to a treatment site can be released to the site through plumbing 2130 and 2150. The action of pump 2140 is responsive to signals generated by control logic 1116, shown in FIG. 11. The disclosed method and apparatus are provided as an implantable system for the delivery of medication or substances locally to a site. However, it can also be engineered to deliver systemically acting substances such as insulin or in response to certain levels of detected substances such as glucose. The ball 2110 can also accommodate one or more actuator devices which release pharmaceuticals and/or bio-pharmaceuticals for gene therapy.

Above are described several embodiments, each of which is a unique method by which a biological molecule may be detected. The descriptions have all used the specific example of glucose, but it should be kept in mind that any biological molecule that undergoes similar enzymatic reactions can also be detected by these same means.

Although the preferred embodiment has been described in detail, it should be understood that various changes, substitutions and alterations can be made therein without departing from the spirit and scope of the invention as defined by the appended claims.

What is claimed is:

1. A biochemical sensor, comprising:
   a ball integrated circuit;
   a sensor media mounted to said ball integrated circuit, said sensor media operable for sensing biochemical molecules;
   a communication link for transmitting data sensed by said sensor media; and
   an attached hydrogel which either collapses or blossoms based upon a polarity on the surface of said ball integrated circuit.

2. The biochemical sensor of claim 1, wherein said communication link is a wireless communication link.

3. The biochemical sensor of claim 2, wherein said ball integrated circuit is externally powered by radio frequency power transmissions, and is only in an active mode to perform sensing functions when energized by said power transmission, and said is then transmitted from the sensor also the sensor also by radio frequency to a distant receiver by said wireless communication link.

4. The biochemical sensor of claim 1, further comprising one or more integrated circuits printed on spherical or non-planar or planar semiconductors for the detection of a single biological molecule by redundant techniques.

5. The biochemical sensor of claim 4, further comprising logic for comparing the redundantly detected data of the same biological molecule to determine if one or sensors is dysfunctional.

6. The biochemical sensor of claim 4, further comprising logic for performing an in situ re-calibration of sensors suspected of drift or biased readings based on sensors that are believed to be responding correctly.

7. The biochemical sensor of claim 1, further comprising one or more integrated circuits printed on spherical or non-planar or planar semiconductors for the detection of several different biological molecules simultaneously.

8. The biochemical sensor of claim 7, further comprising logic to flag chemical imbalances based on detected levels.

9. The biochemical sensor of claim 1, further comprising said sensor media being disposed on a single IC unit.

10. The biochemical sensor of claim 1, wherein said hydrogel which either blossoms or collapses can be controlled to calibrate and test said sensor media.

11. A method of making a biochemical sensor, comprising the step of:

fabricating a ball integrated circuit;

mounting a sensor media to the ball integrated circuit;

sensing biochemical molecules with the sensor media;

transmitting data sensed by the sensor media over a communication link; and attaching a hydrogel to the ball integrated circuit which either collapses or blossoms based upon a polarity on the surface of the ball integrated circuit.

12. The method of claim 11, wherein the communication link in the step of transmitting is a wireless communication link.

13. The method of claim 12, wherein the radio frequency power transmissions externally power the ball integrated circuit and the circuit is only in an active mode to perform sensing functions when energized by the power transmission, and in the step of transmitting, the sensor media also transmits the data by radio frequency to a distant receiver by the wireless communication link.

14. The method of claim 11 further comprising the step of providing one or more integrated circuits printed on spherical or non-planar semiconductors in the step of fabricating for the detection of a single biological molecule by redundant techniques.

15. The method of claim 11 further comprising the step of providing logic, and the step of the logic comparing the data sensed by the sensor media to determine the concentration of the sensed biochemical molecules.

16. The method of claim 11, further comprising the step of providing logic, and the step of the logic performing an in situ re-calibration of the sensor when suspected of drift or biased readings based on one or more other sensors that are believed to be responding correctly.

17. The method of claim 11, further comprising the step of providing one or more integrated circuits printed on spherical or non-planar or planar semiconductors in the step of fabricating for the detection of several different biological molecules simultaneously.

18. The method of claim 11, further comprising the step of providing logic, and the step of the logic flagging chemical imbalances based on detected levels.

19. The method of claim 11, wherein the step of mounting includes mounting the sensor on a single IC unit.

20. The method of claim 11 wherein the hydrogel in the step of attaching can be controlled to calibrate and test the sensor media by either collapsing or blossoming in the presence of a known substance.

* * * * *